United States Patent [19]

Isley

[11] 4,117,717
[45] Oct. 3, 1978

[54] SOLID IMPURITY DETECTOR

[75] Inventor: Walter F. Isley, Grosse Pointe Farms, Mich.

[73] Assignee: Teledyne Industries, Inc., Los Angeles, Calif.

[21] Appl. No.: 809,298

[22] Filed: Jun. 23, 1977

[51] Int. Cl.² ............................................. G01N 15/00
[52] U.S. Cl. ......................................... 73/38; 73/61 R; 116/DIG. 25
[58] Field of Search .................... 73/61 R, 38, 28, 118; 116/114 PV, DIG. 25

[56] References Cited

U.S. PATENT DOCUMENTS

| | | | |
|---|---|---|---|
| 3,033,030 | 5/1962 | Heller | 73/38 X |
| 3,325,010 | 6/1967 | Sackett | 73/38 X |
| 3,413,855 | 12/1968 | Bloom | 73/38 X |
| 3,499,315 | 3/1970 | Marino | 73/38 X |
| 3,583,218 | 6/1971 | Van Nostrand, Sr. | 73/38 X |
| 3,696,666 | 10/1972 | Johnson et al. | 73/38 X |
| 3,939,457 | 2/1976 | Nelson | 73/38 X |
| 4,014,209 | 3/1977 | Emerick | 73/38 X |
| 4,033,733 | 7/1977 | Nelson | 73/38 X |

Primary Examiner—Richard C. Queisser
Assistant Examiner—Joseph W. Roskos
Attorney, Agent, or Firm—Gifford, Chandler, VanOphem, Sheridan & Sprinkle

[57] ABSTRACT

A device is provided for detecting the presence of solid impurities within a pressurized fluid. The device comprises a housing having a fluid passageway formed therein. One end of the fluid passageway is open to the pressurized fluid, preferably via a restricted port, while the other end of the fluid passageway is open to a low pressure fluid region. A filter element is disposed across and obstructs the fluid flow through the passageway at a point intermediate its ends so that the filter element removes solid particles from fluid flowing through the passageway. A pressure sensing means, such as a pressure transducer, communicates with the fluid passageway between the pressurized fluid and the flter element. An increase of fluid pressure sensed by the pressure sensing means is indicative of a clogged filter element which, in turn, indicates the presence of solid impurities within the pressurized fluid. Appropriate indicating means are coupled to the pressure sensing means to provide a signal upon the occurrence of the aforementioned increase of fluid pressure.

6 Claims, 2 Drawing Figures

SOLID IMPURITY DETECTOR

BACKGROUND OF THE INVENTION

I. Field of the Invention

The present invention relates to a device for detecting solid impurities within a pressurized fluid and, more particularly, to such a device which utilizes a filter element and means for measuring an increase in fluid pressure caused by the filter element when clogged.

II. Description of the Prior Art

In internal combustion engines, and particularly turbocharged diesel engines, dust ingestion by the engine has proven to be a very acute problem. Dust ingestion by the engine not only adversely affects the performance of the engine, but also abrades and damages the engine components, most notably the engine pistons, valves, piston rings, and cylinders. Engine damage resulting from dust ingestion, of course, is not only expensive to repair and results in downtime for the engine, but also in the case of military vehicles, an inoperable engine caused by dust ingestion may result in capture of the military vehicle.

In order to prevent, or at least minimize, dust ingestion by the engine, a number of previously known means have been devised to separate dust and other solid particles from the airflow inducted into the engine. For example, filtering systems utilizing filter media are conventionally disposed at the air intake for the engine to separate dust particles from the inducted engine air. A still further type of filtering system for removing dust particles from the inducted air is described in copending application Ser. No. 736,167, Filed on Oct. 27, 1976, and which is commonly owned with the instant application. In any event, all of these previously known systems in one fashion or another remove or separate the dust particles from the air inducted into the engine.

These previously known air filtering systems, however, are prone to failure which subsequently results in the induction of dust particles into the internal combustion engine. For example, filter media often becomes clogged with dust which decreases the efficiency of the filter media which permits dust particles to pass therethrough. At other times the filter media becomes torn or damaged which, likewise, results in dust ingestion by the engine. In either event, the filter media must, at the very least, be cleaned and/or replaced if necessary.

The previously known internal combustion engines, however, have not included means for detecting the failure of the engine filtering system, but rather have relied upon periodic maintenance to inspect the filters. Such periodic maintenance checks, however, often are performed subsequent to the failure of the engine filtering system. Consequently, the engine ingests dust between the time of the failure and the time of the maintenance check. Such dust ingestion, of course, damages the engine in the previously described fashion.

SUMMARY OF THE PRESENT INVENTION

The present invention overcomes the above-mentioned disadvantages by providing a device for detecting solid impurities within a pressurized fluid and which is particularly adapted for use at the air intake of an internal combustion engine.

In brief, the device of the present invention comprises a housing having a fluid passageway formed therein. One end of the fluid passageway is open to a relatively pressurized fluid while the other end of the passageway is opened to a relatively lower pressure region so that fluid flows through the passageway from the high to the lower pressure region. The end connected to the high pressure is provided with a suitable restriction so as to provide a pressure loss at high flow rates. In the preferred form of the invention, one end of the fluid passageway is opened to the outlet of an engine turbocharger while the other end of the passageway is opened to the turbocharger inlet.

A filter element is disposed across the passageway at a point intermediate the ends of the passageway so that the entire fluid flow through the passageway passes through the filter element. The filter element, thus, filters and retains any dust particles or other solid impurities present in the fluid flow.

A pressure sensing means, such as a pressure transducer, communicates with the fluid passageway at a point between the restricted pressure inlet of the passageway and the filter element. The output of the pressure sensing means is coupled to any appropriate means for indicating the magnitude of the pressure within the passageway.

In operation and assuming a relatively clean filter element within the fluid passageway, the pressure sensed by the pressure sensing means remains relatively constant and at a predetermined low magnitude. However, in the event that dust particles or solid impurities are present within the pressurized fluid, these impurities are removed by the filter element from the fluid flow through the passageway. The filter element becomes increasingly clogged with impurities and this creates a back or increased pressure within the fluid passageway which is sensed by the pressure sensing means. The pressure sensing means, in turn, activates the indicating means which warns the operator that a failure of the air filtering system has occurred. The operator can then immediately take appropriate action to either clean, repair, or replace the filtering system in order to prevent damage to the internal combustion engine.

Thus, unlike the previously known internal combustion engines, the device of the present invention provides a means for immediately indicating the failure of the air filtering system for the engine thereby effectively preventing engine damage caused by dust ingestion. Moreover, the device of the present invention is not only inexpensive in construction and installation, but is also virtually fail-safe in operation.

BRIEF DESCRIPTION OF THE DRAWINGS

A better understanding of the present invention will be had upon reference to the following detailed description when read in conjunction with the accompanying drawing wherein like reference characters refer to like parts throughout the several views, and in which.

DETAILED DESCRIPTION OF THE PRESENT INVENTION

Figure 1:
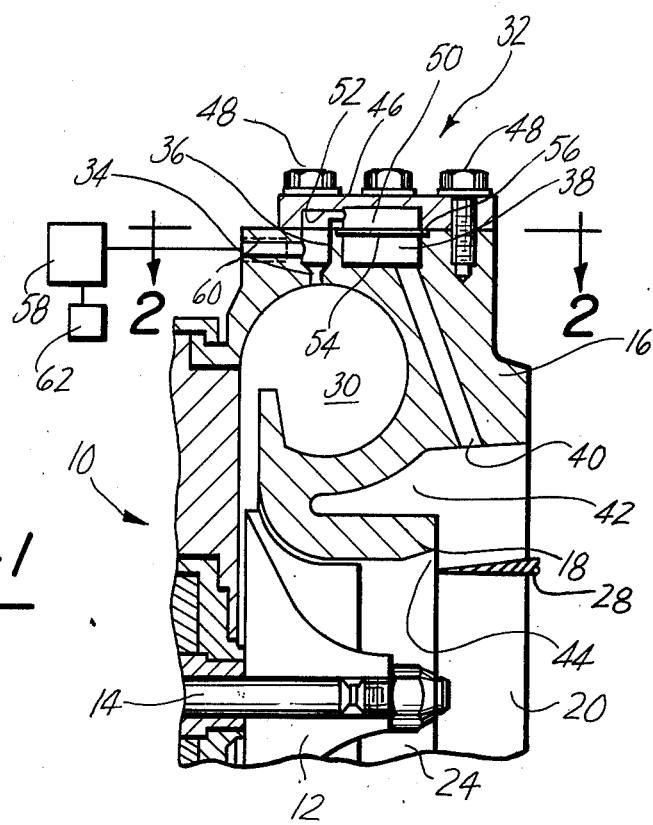
FIG. 1 is a fragmentary cross-sectional view illustrating the device of the present invention operatively installed in the air intake system of an internal combustion engine.
Figure 2:
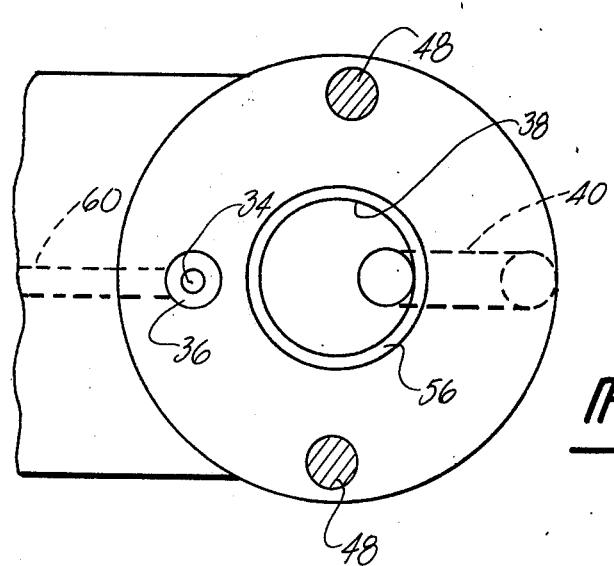
FIG. 2 is a partial sectional view taken substantially along line 2—2 in FIG. 1 and enlarged and with parts removed for clarity.

With reference first to FIG. 1, an engine turbocharger 10 is thereshown having a compressor rotor 12 rotatably mounted on an axle 14 within a turbocharger housing 16. The turbocharger housing 16 also includes an annular housing portion 18 which is concentric with and disposed around the compressor rotor 12.

An air inlet 20 supplies air from an air filtration means (not shown) and to the inlet 24 of the compressor rotor 12. Any conventional air filtration means can be used.

In the operation of the turbocharger 10, as the compressor rotor 12 rotates with the shaft 14, air is inducted through the air inlet 20, from the air filtration means and the fluid passageway 24 to the compressor rotor 12. The compressor rotor 12 compresses the air in an outlet passage 30 and thereafter the compressed air is fed to an internal combustion engine (not shown) by appropriate passages (not shown).

The dust detector 32, according to the present invention, includes a restricted port 34 formed in the turbocharger housing 16 which communicates with the pressurized outlet passage 30. The restricted port 34 in turn opens to an enlarged diameter fluid passage 36 which is opened at its upper end at the exterior of the turbocharger housing 16.

A cylindrical lower filter chamber 38 is formed in the exterior of the tubocharger housing 16 at a position spaced from the passageway 36. The bottom of the lower filter chamber 38 communicates via a fluid passageway 40 with an annular chamber 42 formed within the turbocharger housing 16. In addition, the chamber 42 communicates with the inlet 20 of the compressor.

A housing cover 46 is detachably secured to the turbocharger housing 16 by means of bolts 48 so that the cover 46 covers and encloses the passageway 36 and lower filter chamber 38 within the turbocharger housing 16. An upper filter chamber 50 is formed within the cover 46 which registers with the lower filter chamber 38. In addition, a fluid passageway 52 is also provided within the cover 46 which is open at one end to the passageway 36 in the turbocharger housing 16 and at its other end to the upper filter chamber 50. With the cover 46 secured to the turbocharger housing 16 in the previously described fashion, a fluid passageway 55 comprising the port 34, passageways 36 and 52, the filter chambers 50 and 38, and the passageway 40 is formed between the compressor rotor outlet 30 and its inlet 24.

A preferably disposable filter element 54 is positioned across and between the upper and lower filter chambers 50 and 38, respectively. The filter element 54 extends entirely across the filter chambers 50 and 38 so that the entire fluid flow through the filter chambers 50 and 38 passes through the filter 54. Although the filter element 54 can be constrained between the filter chamber 50 and 38 in any desired fashion, preferably an annular mounting groove 56 is formed around the upper end of the lower filter chamber 38 so that the filter element 53 rests along the groove 56. In addition, the depth of the groove 56 is preferably less than the thickness of the filter element 54 so that upon attachment of the cover 46 to the turbocharger housing 16, the filter element 54 is compressed and thereby rigidly secured between the filter chambers 38 and 50.

A pressure transducer 58 communicates with the fluid passageway between the pressurized outlet 30 and the filter element 54 and preferably communicates with the fluid passageway 36 by means of a transverse intersecting passageway 60. The transducer 58 produces an output signal representative of the fluid pressure within the passageway 36 and appropriate indicating means 62 are coupled to the transducer means 58 to provide a signal representative of the transducer output.

The component parts of the dust detector 32 of the present invention having been described, the operation is as follows:

Assuming normal engine operation, air is inducted by the compressor rotor 12 through the inlet 20, from the air filtration means. The rotor 12 compresses this inlet air within the chamber 30 and the compressed air is then fed to the engine in the previously-described fashion.

Due to the high pressure within the chamber 30, a portion of this air expands through the restricted port 34, the filter chambers 50 and 38, the filter element 54, and to the relatively low pressure chamber 42 in communication with the inlet 20. The air pressure at the outlet 30 of the compressor rotor 12, of course, exceeds the air pressure at the rotor inlet 20.

Further assuming that the air filtration means (not shown) is functioning in its proper and intended fashion, the air inlet provides only clean or dust-free air at the compressor rotor inlet 24. Consequently, the airflow through the dust detector 32 is also dust free and the air pressure sensed by the transducer means 58 remains within predetermined limits.

In the event of failure of the air filtration means (or equivalent failure), dust-laden air will be supplied to the compressor rotor inlet 24. The compressor rotor 12 compresses the dust-laden air within the outlet 30 and a portion of this dust-laden air flows through the passageway 55 of the dust detector 32. The filter element 54 filters or removes the dust particles from the airflow in the conventional fashion.

As the filter element 54 becomes increasingly clogged with dust particles, a back or increased pressure is created between the filter element 54 and the restricted port 34. This increase of fluid pressure is detected by the pressure transducer means 58 which generates appropriate signals to the indicating means 62. The indicating means 62 in turn signals the operator that the pressurized air in the outlet 30, and consequently the air that is supplied to the engine, is dust-laden whereupon the operator can immediately shut down the engine and service the air filtration means. Following the required maintenance on the air filtration system, the cover 46 is removed from the housing 16 and the filter element 54 is either cleaned or replaced by a clean filter element. After the cover 46 is resecured to the housing 16 by the bolts 48, the dust detector 32 is again in a fully operational condition.

The dust detector 32 of the present invention, thus, provides a simple and economical means for detecting the presence of dust or other solid impurities in the pressurized air in the turbine blade outlet 30. By early detection of dust in the passageway 30, prolonged dust ingestion by the engine can be avoided, thus, protecting the engine against damage caused by dust ingestion.

A still further advantage of the dust detector 32 of the present invention is that the filter element 54 can be easily, readily, and inexpensively replaced or cleaned after clogging caused by dust ingestion.

While the dust detector 32 has been described for use with an engine turbocharger, it will be understood, of course, that the dust detector 32 can be used in conjunction with any pressurized fluid sufficient to cause a fluid flow through the passageway 55 of the dust detector 32.

Having described my invention, many modifications thereto will become apparent to those skilled in the art to which it pertains without deviating from the spirit of the invention as defined by the scope of the appended claims.

What is claimed is:

1. A device for detecting solid impurities in a pressurized fluid comprising;
    a housing;
    a fluid pump in said housing, said fluid pump having a high pressure outlet and a low pressure inlet;
    said housing having a fluid passageway open at its first end to the pump outlet and open at its second end to a chamber formed annularly around the pump inlet, said annular chamber being open to the pump inlet;
    a filter element disposed across and covering said fluid passageway; and
    pressure sensing means in communication with said passageway between its first end and said filter element.

2. The invention as defined in claim 1 wherein said fluid pump is a compressor rotor for a turbocharger of an internal combustion engine.

3. The invention as defined in claim 1 in which the first end of the fluid passageway opens to the pressurized fluid through a restricted port.

4. The invention as defined in claim 1 wherein said housing comprises a first part detachably secured to a second part and wherein the filter element is sandwiched between the housing parts.

5. The invention as defined in claim 4 wherein one of said housing parts forms a portion of a housing for the fluid pump.

6. The invention as defined in claim 1 and including an annular housing portion formed around the pump inlet, a fluid inlet housing having an annular air inlet passageway formed therein, said fluid inlet housing being spaced radially inwardly and extending away from said annular housing portion wherein an annular opening is formed between said annular housing portion and said fluid inlet housing.

* * * * *

UNITED STATES PATENT AND TRADEMARK OFFICE
CERTIFICATE OF CORRECTION

PATENT NO. : 4,117,717
DATED : October 3, 1978
INVENTOR(S) : Walter F. Isley

It is certified that error appears in the above-identified patent and that said Letters Patent are hereby corrected as shown below:

Abstract, line 13, delete "flter" and insert --filter-- therefor;

Column 3, line 49, insert --element-- after "filter" and before "54";

Column 3, line 53, delete "53" and insert --54-- therefor.

Signed and Sealed this

Sixth Day of February 1979

[SEAL]

Attest:

RUTH C. MASON
Attesting Officer

DONALD W. BANNER
Commissioner of Patents and Trademarks